United States Patent [19]
Weissgerber

[11] Patent Number: 4,911,405
[45] Date of Patent: Mar. 27, 1990

[54] VALVE UNIT

[75] Inventor: Hans-Georg Weissgerber, Waldbronn, Fed. Rep. of Germany

[73] Assignee: Hewlett-Packard Co., Pato Alto, Calif.

[21] Appl. No.: 305,885

[22] Filed: Feb. 2, 1989

[30] Foreign Application Priority Data

Feb. 13, 1988 [EP] European Pat. Off. ........... 88102151

[51] Int. Cl.⁴ .................... F04B 39/08; F16K 31/10
[52] U.S. Cl. ..................... 251/129.14; 251/129.17; 251/129.19; 251/368; 137/901; 417/505
[58] Field of Search .............. 251/129.14, 129.17, 251/129.19, 368; 137/901; 417/505

[56] References Cited

U.S. PATENT DOCUMENTS

| | | | |
|---|---|---|---|
| 1,146,850 | 7/1915 | Cullum | 137/901 X |
| 2,031,478 | 2/1936 | Gray | 251/129.14 X |
| 2,735,047 | 2/1956 | Garner et al. | 251/129.19 X |
| 2,868,494 | 1/1959 | Kearns, Jr. et al. | 251/129.14 X |
| 3,819,305 | 6/1974 | Klochemann et al. | 417/505 X |
| 3,887,162 | 6/1975 | Antoni et al. | 251/368 X |
| 4,057,216 | 11/1977 | Flaschar et al. | 137/901 X |
| 4,228,821 | 10/1980 | Stark | 251/368 |
| 4,297,083 | 10/1981 | von Petery | 417/505 X |
| 4,344,743 | 8/1982 | Bessman et al. | 417/505 X |

FOREIGN PATENT DOCUMENTS

| | | | |
|---|---|---|---|
| 2107371 | 9/1971 | Fed. Rep. of Germany | 417/505 |
| 2411285 | 9/1974 | Fed. Rep. of Germany | 251/129.14 |

Primary Examiner—John Rivell

[57] ABSTRACT

A valve unit, in particular for use at the suction inlet of a pumping apparatus, comprises a ball valve having a ball (2) and a seat (1) for controlling the flow of liquid between an inlet (18) and an outlet (19). A spring (3) forces the ball (2) into the seat (1). An actuating pin (8) projects through the valve seat (1) and contacts the ball (2). The actuating pin (8) is designed such that liquid can pass alongside the pin through a passageway (22). The armature (14) of a solenoid (12) can be pushed against a membrane (10) which is in contact with the actuating pin (8) so that the ball (2) is lifted from the seat (1) and the valve is opened. Since the opening and the closing of the valve unit can thus be actively controlled, the switching operation of the valve unit is very well reproducable resulting in a more uniform flow of the liquid delivered by a pumping apparatus connected to the outlet (19) of the valve unit.

11 Claims, 2 Drawing Sheets

VALVE UNIT

TECHNICAL FIELD

The invention relates to a valve unit, in particular an inlet valve arranged at the suction inlet of a pumping apparatus, e.g., a piston pump having one or several pistons. Such an inlet valve enables flow of liquid from a liquid supply into the pump during the intake stroke of the pump and it prevents that liquid delivered during the expulsion stroke is fed back to the supply. A field of application for such an inlet valve are pumps used in liquid chromatography for compressing and delivering liquid to the chromatographic column.

BACKGROUND ART

A valve unit 1 is known from US-A-3,810,716. In this publication, a pumping apparatus for a liquid chromatograph is disclosed which comprises a pump head with a bore and a piston for reciprocation within the bore. Check valves are provided at the suction inlet and at the outlet of the pump. The check valves comprise a ball and a corresponding seat and a surrounding housing which confines the movement of the ball. When liquid pushes against the ball from the side opposite the bearing face of the ball, the ball rises from the seat so that the valve is opened. When liquid pushes against the ball from the opposite side, the valve is closed. In the pumping apparatus, the check valves are arranged such they prevent backflow of the sucked in and of the delivered liquid ; forcing the liquid being pumped to flow in the desired direction. Thus, during the suction stroke of the pump, the inlet check valve is open and the outlet check valve is closed; during the delivery stroke of the pump it is just the other way round.

The opening and closing behaviour of a check valve, e.g., the distance by which the ball is raised from the seat or the switching time of the valve, depends on the flow rate and pressure of the liquid through the valve, the viscosity of the liquid and other parameters. Thus, the operation of such a valve is not completely reproducible which can result in variations of the flow of the liquid delivered by the pumping apparatus. Such variations are particularly disturbing in high performance liquid chromatography, because they would impair the accuracy of the chromatographic measuring results.

Relative to the above described prior art, it is an object of the invention to provide a valve unit, in particular for a pumping apparatus, which has a higher reproducibility of its opening and closing operation ensuring a more uniform flow of the liquid delivered by the pumping apparatus.

SUMMARY OF THE INVENTION

This object is achieved according to a preferred embodiment of the invention, in which the check valve at the suction inlet of the pumping apparatus is replaced by an active inlet valve which can be opened or closed via controllable actuating means and is therefore not dependent on the imponderabilities in the operation of a check valve . The valve unit according to a preferred embodiment of the invention comprises a ball valve with a valve ball and a corresponding valve seat and an actuating element for lifting the ball off the seat in order to open the valve. Thus, the opening and closing of the valve can be precisely controlled and the switching times of the valve are kept small, resulting in a more constant flow rate of the liquid delivered by the pumping apparatus. Typical switching times are in the range of less than 3 milliseconds. If the invention is used in a liquid chromatograph , the constant flow rate achieved ensures high reproducibility of the chromatographic measuring process. According to a further advantage of the invention which is particularly essential for liquid chromatography, the valve unit has a low dead volume and it can easily be flushed since it is substantially free of zones where residues of liquid or gas bubbles might accumulate. Due to the low dead volume and the easy flushing of the valve, the invention permits faster changes of solvent gradients and therefore a higher efficiency of the chromatographic process when low pressure gradient operation is performed wherein several types of liquids are mixed before reaching the pumping apparatus.

It is understood that the invention is not limited to a ball valve but that other types of actively controlled valves are possible, for example a conical plug and a corresponding seat into which the plug can be moved for closing the valve. It is furthermore understood that the valve unit according to the invention can be used not only at the inlet of a pumping apparatus, but also at other locations in a liquid transporting system where reproducibility and reliability of the valve operation is essential. The valve unit could for example be used as a flushing valve in a liquid chromatograph.

The invention has the further advantages that the switching times of the valve are independent of the type of liquid flowing through the valve, so that the reproducibility of the valve does not suffer from a change of the type of liquid being pumped. Furthermore, no backflow of liquid is required for the closing of the valve, and the valve operation is independent of the spatial position of the valve, in contrast to some prior art valves wherein gravity provides the restoring force for the valve. Also, the motion of the valve ball in an embodiment of the invention is independent of the flow rate, solvent viscosity and other parameters of the liquid, thus also contributing to a higher reproducibility. Furthermore, the susceptibility to contamination of the valve is low and it can easily be flushed. If the valve ball is sticking to the seat, which may happen when salt solutions have passed through the valve and the valve has not been flushed by liquid for a long time so that salt crystals have deposited, the invention permits to open the valve again, whereas this would not be possible with check valves. By the controllable actuation of a valve unit of the invention, it is avoided that the two sealing partners, e.g. the ball and the seat, are sticking when they should be charged electrostatically, a phenomenon which may occur with certain solvents and with certain materials, for example sapphire and ruby.

According to an embodiment of the invention, the actuation of the actuating element for pushing out the ball of the seat may occur by applying a resilient force, e.g., by the use of a spring. The magnitude of the resilient force, e.g., the spring constant, is selected such that the ball can only be pushed out of the seat when the pressure in the liquid at the other side of the ball is below a certain value. Otherwise, if the valve would open immediately at the beginning of the suction stroke of the pump, the liquid in the pump would suddenly expand which may lead to the formation of gas bubbles, particularly with low-boiling liquids.

Subsequently, an embodiment of the invention is explained in more detail with reference to the drawings.

BEST MODE FOR CARRYING OUT THE INVENTION

Figure 1:
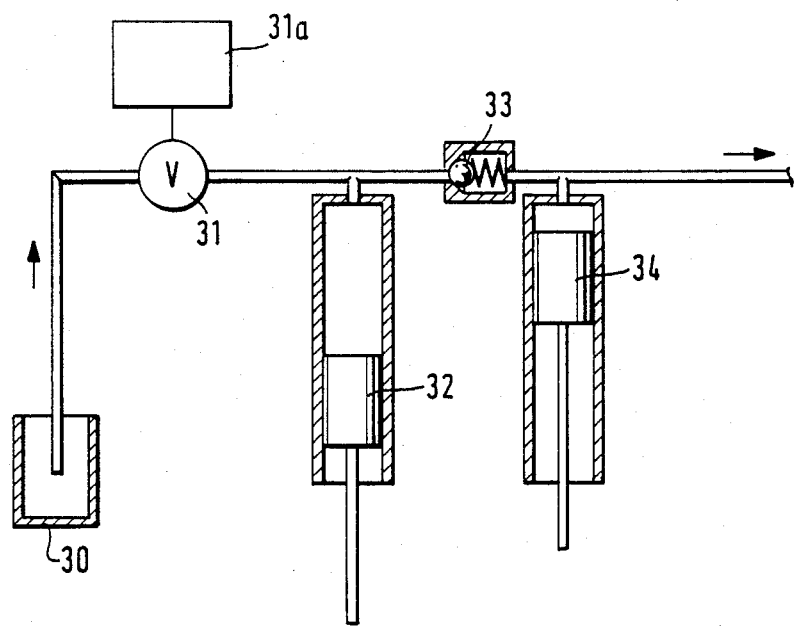
FIG. 1 schematically shows a pumping apparatus for delivering liquid at high pressure incorporating a valve unit according to the invention.

FIG. 1 schematically depicts a pumping apparatus for delivering liquid at high pressure of the type that is used in a liquid chromatograph for delivering solvent to the chromatographic column. The pumping apparatus shown is a two-piston pump with two serially connected pump heads, each comprising a piston 32, 34 and having an inlet valve 31 according to the invention at the inlet of the first pump head and a check valve 33 between the first and the second pump head. The inlet valve 31 is an active valve which can be opened or closed under external control by means of an actuating mechanism schematically indicated by block 31a. The check valve 33 is a passive valve which permits flow of liquid from the first to the second pump head and which inhibits flow of liquid in the reverse direction. The check valve 33 may comprise a spring for urging the valve ball into the valve seat. The solvent to be delivered is contained in a reservoir 30 and is sucked in when the first piston 32 retracts provided the inlet valve 31 is opened. In the example shown, the pistons 32,34 operate with a phase difference of 180 degrees, that means the piston 34 is at its top dead centre when the piston 32 is at its bottom dead centre and vice versa. The stroke volume of the first piston is larger than the stroke volume of the second piston; preferably, the stroke volume of the second piston is half the stroke volume of the first piston. In that way, a substantially smooth flow of the liquid delivered by the pumping apparatus to the chromatographic system can be achieved.

It is understood that the invention is not limited to a pumping apparatus as shown in FIG. 1. Instead of the serial connection of the pistons shown, a parallel connection of the pistons could also be used, or several pistons or only one piston. Furthermore, the invention might also be used with different types of pumps, for example with diaphragm pumps.

In the following, the inlet valve 31 schematically depicted in FIG. 1 is explained in detail with reference to FIG. 2. An inlet port 18 can be connected to the reservoir 30 and an outlet port 19 can be connected to the first pump head of the pumping apparatus as shown in FIG. 1. Inside the valve, liquid flows from the inlet port 18 via a passageway 20 to a cavity 21 which is sealed off at one side by a membrane 10. From this cavity, liquid can flow through a passageway 22 and a ball valve (provided it is opened) comprising a ball 2 and a corresponding seat 1 to the outlet port 19.

The seat 1 and the ball 2 of the ball valve are preferably made of a hard material, e.g., a sapphire or ceramic seat and a ruby ball. The ball 2 is pressed into the seat 1 by the spring 3 which is preloaded as shown in FIG. 2. The seat 1 is jammed between an insert element 4 and a valve body 5. Sealing washers 6, 7 are provided between the insert element 4 and the seat 1 as well as between the valve body 5 and the seat 1, respectively. The insert element 4, together with the seat 1, the ball 2, the spring 3, and the sealing washer 6 are pressed into place in the valve body 5 such that the seat is in contact with the sealing washer 7. Instead of the press fit just described the insert element 4 and the body 5 could also be welded or glued together.

Figure 2:
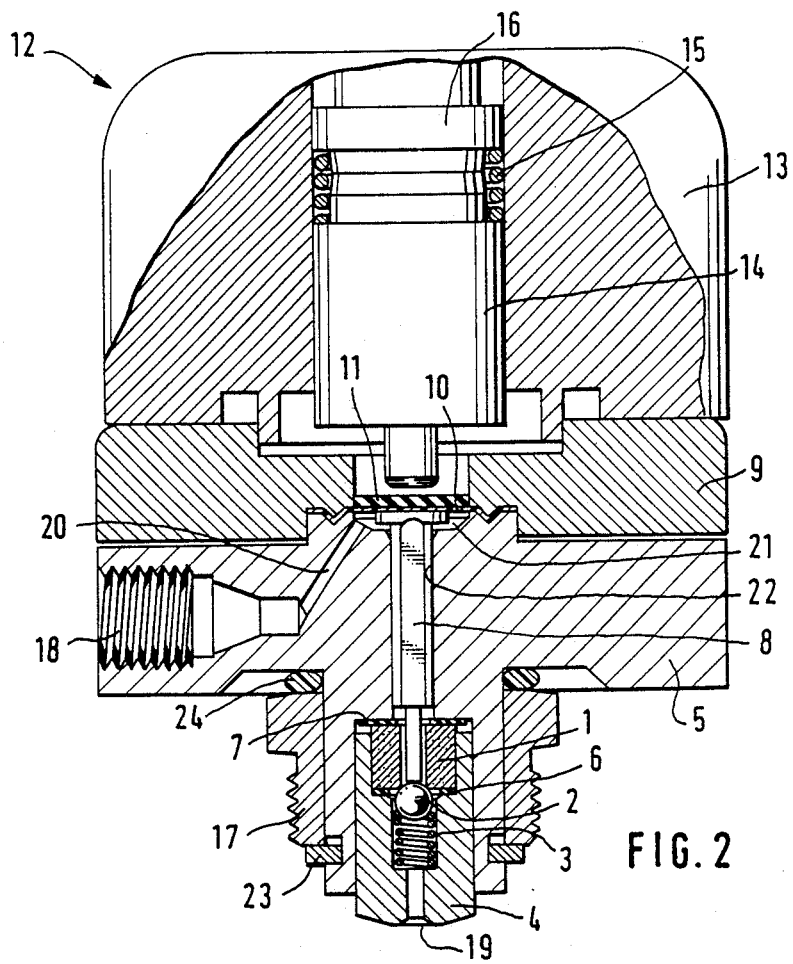
FIG. 2 is a cross section of a valve unit according to an embodiment of the invention.

In FIG. 2, the ball valve is shown in its closed state. The valve can be opened by means of an actuating pin 8 which extends from the cavity 21 through the passageway 22 and the seat 1 to the ball 2. The actuating pin 8 comprises a head located in the cavity 21. Details of the pin head are explained in more detail below with reference to FIG. 3. The portion of the pin extending into the passageway 22 has a substantially rectangular cross section with the longer side being somewhat smaller than the cross section of the passageway 22 such that the pin can be moved in the passageway 22. Due to the substantially rectangular cross section of the pin 8, liquid can flow through the passageway in the gap between the pin and the wall of the passageway. At its lower end, the pin narrows and extends through the seat 1 of the ball valve and touches the ball 2. The diameter of the portion of the pin inside the seat is selected such that liquid can flow between the pin and the inner wall of the seat.

The screw 17 and the snap ring 23 serve for adaptation of the valve to a pump head. The gasket 24 provides a frictional resistance connection between the screw 17 and the valve body 5.

The cavity 21 wherein the head of the actuating pin is located is sealed off by a membrane 10. The membrane 10 is clamped between the valve body 5 and an adapter plate 9. The valve body 5 comprises a V-shaped groove and the adapter plate 9 comprises a corresponding counterpart with the membrane being clamped between these two mating parts such that it is kept stretched. On the other side of the membrane 10 is arranged a rubber plate 11 which serves as a damping element in the actuation of the pin 8.

The pin 8 is actuated by a solenoid 12 which is connected to the adapter plate 9, e.g., by means of screws. The solenoid comprises a housing 13, an armature 14, a spring 15 and a stop 16. The electrical coil necessary for the activation of the solenoid is arranged in the housing 13. When the solenoid is activated, the armature 14 is pulled against the resilient force of the spring 15 towards the stop 16. Consequently, no force is exerted by the armature on the actuating pin 8 so that the ball 2 of the ball valve is pressed into the seat 1 by the spring 3, thus keeping the valve closed. When the valve is to be opened, the solenoid is deactivated so that the spring 15 pushes the armature 14 against the rubber plate 11 leading to a displacement of the actuating pin 8 away from the armature. Due to this displacement, the ball 2 is lifted off the seat 1 so that the valve is opened. The maximum distance by which the ball 2 can be lifted off the seat 1 corresponds to the distance between the lower edge of the head of the pin 8 and the wall of the cavity 21 when the armature exerts no force on the rubber plate 11. According to a practical example, this distance and therefore the travel of the ball 2 is 0,2 mm. The gap between the armature 14 and the rubber plate 11 is adjustable by corresponding adjustment of the stop 16. In a practical example of the invention, this gap is 0,1 mm. The solenoid used in the embodiment according to FIG. 2 may be a conventional solenoid except that the spring constant of the spring 15 is specially selected as will be explained below in more detail.

Figure 3:
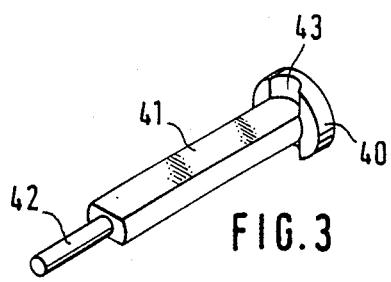
FIG. 3 is a perspective view of the actuating pin of the valve unit according to FIG. 2.

In the following, the actuating pin 8 is described in more detail with reference to FIG. 3. The actuating pin substantially comprises three regions: a pin head 40, a centre piece 41, and an end piece 42. When the pin is inserted in the inlet valve, the pin head 40 is arranged in the cavity 21 (FIG. 2) such that its top face is in contact with the membrane 10, the centre piece 41 is arranged in the passageway 22, and the end piece 42 in the central bore of the valve seat 1 such that its bottom face is in contact with the ball 2 of the ball valve. The pin head 40 has a recess 43 which ensures that when the pin head has been pushed by the armature 14 against the valve body 5, liquid can flow from passageway 20 and cavity 21 into passageway 22. The centre piece 41 of the pin has a substantially rectangular cross section such that liquid can flow through passageway 22 when the pin is inserted. The end piece 42 has a circular cross section and is dimensioned such that sufficient space is left for the passage of liquid through the bore. It is understood that various modifications of the design of the actuating pin are possible.

In the following, the operation of the valve according to the invention is explained in connection with a piston pump whereby the valve is arranged at the inlet of the pump (see FIG. 1). The control of the valve and the pump are synchronized such that at the beginning of the suction stroke of the pump, the electric current through the coil of the solenoid is interrupted so that the magnetic field of the solenoid collapses and the spring 15 pushes the armature into the direction of the ball valve. As a consequence thereof, the armature strikes the rubber plate 11. The rubber plate 11 dissipates the kinetic energy of the armature and thereby protects the membrane 10.

At the beginning of the suction stroke, the pressure in the pump still is at an increased level resulting from the preceding compression/expulsion stroke. This increased pressure is also present at the ball valve since there is an hydraulic connection to the pump. The pressure created by a pumping system in high performance liquid chromatography typically ranges to 400 bar ($4.10^7$ PA). According to an embodiment of the invention, the spring 15 has such a spring constant that, even if the solenoid has been deactivated so that the armature is free to move, the ball valve is not opened as long as the pressure in the pump is larger than approximately 10 bar ($10^6$ Pa). In that case, the force of the spring 15 is not sufficient to lift via the actuating pin 8 the ball 2 from the seat 2 against the counterforce exerted on the ball from the other side by the pressurized liquid. By this dimensioning of the springs, a sudden expansion of the pressurized liquid is avoided.

When the piston is further retracting in the course of its intake stroke, the pressure in the pump is further reduced. At about 10 bar, the force exerted on the ball 2 by the liquid is so small that the pin 8 can lift the ball out of its seat. Thereby, the armature 14, the rubber plate 11, the membrane 10 and the pin 8 are moved by distance corresponding to the valve lift of the ball. Now, the pump can suck in liquid through the valve.

When the piston 32 is at its bottom dead centre and starts changing its direction of movement, the solenoid is activated again by supplying it with current so that the armature 14 is pulled back towards the stop 16. Since there is no counterforce, the spring 3 presses ball 2 back into its seat so that the pin 8, the membrane 10, and the rubber plate 11 are pushed back to their original position. Now, the valve is closed, the pump can build up pressure and then deliver the pressurized liquid to the chromatographic system. When the piston is back in its top dead centre, the above-described cycle starts anew.

I claim:

1. An actively controlled valve operationally responsive to cyclical phases of a pump, the valve comprising:
   a valve body having an inlet and an outlet, the valve body defining a fluid passageway between the inlet and the outlet;
   regulating means disposed within the fluid passageway for allowing and preventing fluid flow therethrough;
   sensing means for determining selected points of the cyclical phases of a pump coupled to the valve body, and for generating a signal when each of the selected points are determined; and
   actuating means joined to the valve body and operationally coupled to the regulating means for actively controlling said regulating means, the actuating means including kinetic energy dampening means for providing dampened coupling to the regulating means, the actuating means further being in signal responsive communication with the sensing means.

2. The valve of claim 1 wherein said regulating means includes a ball check valve having an open position and a closed position, and including biasing means for urging the ball towards the closed position, the biasing means exerting a first force on the ball when in the closed position.

3. The valve of claim 2 wherein said actuating means includes a solenoid having an armature biased between an activated position and a de-activated position, and including a pin having a first end contacting said ball and a second end being in operational contact with the armature, said kinetic energy dampening means including a resilient member disposed between the second end and the armature to dampen the kinetic energy of the armature when brought into contact with the resilient member while moving to said de-activated position, the armature when in the de-activated position exerting via the pin a second force on said ball opposite to said first force.

4. The valve of claim 3 wherein said second force is insufficient to overcome said first force and a fluid pressure above a predetermined level, which fluid pressure acts on the same side of the ball as said first force.

5. The valve of claim 4 wherein said biasing means in said ball valve includes a first spring, and wherein said armature is biased by a second spring.

6. The valve of claim 4 wherein said predetermined level of fluid pressure is not greater than 10 bars.

7. The valve of claim 1 wherein said pump is a piston pump having a piston and a chamber, and said sensing means determines the position of the piston and communicates a signal to said actuating means when the piston is at top dead center and bottom dead center.

8. A fluid delivery system comprising:
   a valve unit including,
   (i) a valve body that defines an inlet, an outlet and a fluid passageway therebetween,
   (ii) fluid regulating means disposed within the fluid passageway for allowing and preventing fluid flow therethrough,
   (iii) actuating means joined to the valve body and operationally coupled to the regulating means for actively controlling said regulating means, the actuating means including kinetic energy dampening means for providing dampened coupling to the regulating means;

a liquid source connected to the inlet of the valve unit;

a delivery line connected to the outlet of the valve unit;

a plurality of pumps connected to the delivery line, each pump having a corresponding pump operating 180° out of phase of each other; and sensing means for determining selected cyclical phases of said pumps and for generating a signal when each of the selected cyclical phases are determined, the sensing means being in signal communication with the actuating means such that the actuating means is activated and de-activated in response to the signals.

9. The system of claim 8 wherein said regulating means includes a ball check valve having an open position and a closed position, and including biasing means for urging the ball towards the closed position, the biasing means exerting a first force on the ball when in the closed position, and wherein said actuating means includes a solenoid having an armature biased between an activated position and a de-activated position, and including a pin having a first end contacting said ball and a second end being in operational contact with the armature, said kinetic energy dampening means including a resilient member disposed between the second end and the armature to dampen the kinetic energy of the armature when brought into contact with the resilient member while moving to said de-activated position, the armature exerting via the pin a second force on said ball opposite to said first force, when the armature is in the deactivated position.

10. The valve of claim 9 wherein said second force is insufficient to overcome said first force and a fluid pressure above a predetermined level, which fluid pressure acts on the same side of the ball as said first force.

11. A fluid delivery system comprising:
a valve unit including,
(i) a valve body that defines an inlet, an outlet and a fluid passageway therebetween,
(ii) a ball and seat check valve disposed within the fluid passageway, the ball being movable between an open and a closed position with a first spring urging the ball towards the closed position by applying a first force on the ball,
(iii) a solenoid connected to the valve body and operationally coupled to the ball via a pin disposed in the fluid passageway, the solenoid having an armature movable between an activated position and a de-activated position, and having a second spring to urge the armature towards the de-activated position and to apply a second force opposite the first force to the ball, the pin having a first end contacting the ball and a second end being coupled to the armature through a resilient member that dampens the kinetic energy of the armature, the second force being insufficient to overcome the first force and a fluid pressure above a prescribed level acting on the same side of the ball as the first force;

a liquid source connected to the inlet of the valve unit;

a delivery line connected to the outlet of the valve unit;

a pump connected to the delivery line, the pump including a first piston and pumping chamber having a first stroke volume, and including a second piston and pumping chamber having a second stroke volume, the second stroke volume being one half the first stroke volume, each of the pumping chambers being connected serially to the delivery line with the first pumping chamber closest to the outlet of the valve unit and with a check valve disposed in the delivery line between the first and second pumping chambers, the first and second pistons being 180° out of phase with each other; and sensing means for determining when the first piston reaches top dead center and bottom dead center, and for generating a signal when each position is reached by the first piston, the solenoid being in signal receiving relation with the sensing means such that the solenoid is activated when the first piston reaches bottom dead center and is deactivated when the first piston reaches top dead center.

* * * * *